United States Patent
Lee et al.

(10) Patent No.: US 11,608,307 B2
(45) Date of Patent: Mar. 21, 2023

(54) METHOD FOR PREPARING ALKYL CARBOXYLIC ACID ESTER AND APPARATUS FOR PREPARING ALKYL CARBOXYLIC ACID ESTER

(71) Applicant: GS CALTEX CORPORATION, Seoul (KR)

(72) Inventors: Kyoung Jun Lee, Daejeon (KR); In Chang Choi, Daejeon (KR); Woo Young Kim, Chungcheongbuk-do (KR)

(73) Assignee: GS CALTEX CORPORATION, Seoul (KR)

( * ) Notice: Subject to any disclaimer, the term of this patent is extended or adjusted under 35 U.S.C. 154(b) by 0 days.

(21) Appl. No.: 17/296,083

(22) PCT Filed: Nov. 25, 2019

(86) PCT No.: PCT/KR2019/016270
§ 371 (c)(1),
(2) Date: May 21, 2021

(87) PCT Pub. No.: WO2020/106123
PCT Pub. Date: May 28, 2020

(65) Prior Publication Data
US 2022/0009872 A1  Jan. 13, 2022

(30) Foreign Application Priority Data

Nov. 23, 2018 (KR) .................. 10-2018-0146734

(51) Int. Cl.
*C07C 67/08* (2006.01)
*C07C 67/54* (2006.01)

(52) U.S. Cl.
CPC .............. *C07C 67/08* (2013.01); *C07C 67/54* (2013.01)

(58) Field of Classification Search
CPC ......... C07C 67/08; C07C 67/54; C07C 69/68;
H01G 13/00; H01G 13/006; H01G 4/005;
H01G 4/012; H01G 4/12; H01G 4/1209;
H01G 4/224; H01G 4/232; H01G 4/248;
H01G 4/30
See application file for complete search history.

(56) References Cited

U.S. PATENT DOCUMENTS 8,895,765 B2 * 11/2014 Kim .................. C11C 3/003
422/600
2016/0194267 A1 * 7/2016 Backes .................. B01D 3/002
560/1

FOREIGN PATENT DOCUMENTS

| KR | 10-1995-0013081 B1 | 10/1995 |
| KR | 10-2005-0084179 A | 8/2005 |
| KR | 10-2008-0036107 A | 4/2008 |
| KR | 10-1136783 B1 | 4/2012 |
| WO | WO 2015/036747 A1 | 3/2015 |

OTHER PUBLICATIONS

International Search Report for PCT/KR2019/016270 dated Mar. 25, 2020.

* cited by examiner

*Primary Examiner* — Yevgeny Valenrod
*Assistant Examiner* — Blaine G Doletski
(74) *Attorney, Agent, or Firm* — The PL Law Group, PLLC

(57) ABSTRACT

In methods for preparing an alkyl carboxylic acid ester according to embodiments of the present invention, a first reaction product is produced by reaction of a carboxylic acid stream and a first alcohol stream in a preliminary reactor. A second reaction product is produced by at least partially removing alcohol and water from the first reaction product. The second reaction product is esterified by reaction with a second alcohol stream in a main reactor. An alkyl carboxylic acid ester is recovered from the main reactor.

9 Claims, 6 Drawing Sheets

METHOD FOR PREPARING ALKYL CARBOXYLIC ACID ESTER AND APPARATUS FOR PREPARING ALKYL CARBOXYLIC ACID ESTER

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2019/016270, filed Nov. 25, 2019, which claims priority to the benefit of Korean Patent Application No. 10-2018-0146734 filed in the Korean Intellectual Property Office on Nov. 23, 2018, the entire contents of which are incorporated herein by reference.

BACKGROUND

1. Technical Field

The present invention relates to a method for preparing an alkyl carboxylic acid ester and an apparatus for preparing an alkyl carboxylic acid ester. More particularly, the present invention relates to a method for preparing an alkyl carboxylic acid ester through the esterification reaction of an alcohol and a carboxylic acid and an apparatus for preparing an alkyl carboxylic acid ester.

2. Background Art

For example, alkyl carboxylic acid esters such as ethyl lactate are widely used as solvents of all kinds of polishing solutions, etching solutions, photosensitive resin compositions, resist compositions, etc., in the manufacturing process of semiconductors or manufacturing process of displays.

In case of the manufacturing process of semiconductors, requiring the degree of precision of tens or several nano scale, all components of a composition are required to have high purity, and if a small quantity of impurities are included, the reliability of the whole manufacturing process of semiconductors may be deteriorated. Accordingly, the secure of ethyl lactate with high purity, used in a fine process is required.

Ethyl lactate may be obtained through, for example, the esterification reaction of lactic acid and ethanol. Lactic acid may be obtained by bio-based synthesis through fermentation reaction using microorganism.

In this case, the raw material of lactic acid may include impurities derived from microorganism, fermentation raw materials, etc., and accordingly, the purity and selectivity of ethyl lactate may be reduced. In addition, the purity and selectivity of ethyl lactate may also be reduced by impurities through the self-reaction of lactic acid.

Accordingly, for the synthesis process of ethyl lactate with high purity and high selectivity, the reactor is also required to be designed to have high selectivity and high capacity for esterification reaction, and the use of ethanol with high purity is required. In this case, the load of a reactor may be excessively increased, and high cost may be consumed.

For example, in Korean Laid-open Patent Publication No. 2005-0084179, a continuous-type method for preparing ethyl lactate is disclosed, but as described above, research on design for an esterification reaction process, by which impurities are removed from lactic acid, and economic feasibility is improved, is required.

SUMMARY

A task of the present invention is to provide a method for preparing an alkyl carboxylic acid ester having excellent purity and selectivity.

Another task of the present invention is to provide an apparatus for preparing an alkyl carboxylic acid ester having excellent purity and selectivity.

1. A method for preparing an alkyl carboxylic acid ester, the method comprising: reacting a carboxylic acid stream and a first alcohol stream in a preliminary reactor to produce a first reaction product; at least partially removing alcohol and water from the first reaction product to produce a second reaction product; esterifying by reacting the second reaction product with a second alcohol stream in a main reactor; and recovering an alkyl carboxylic acid ester from the main reactor.

2. The method for preparing an alkyl carboxylic acid ester according to above 1, wherein the at least partial removing of the alcohol and water is performed through a distillation column.

3. The method for preparing an alkyl carboxylic acid ester according to above 1, wherein the production of the first reaction product in the preliminary reactor comprises converting a portion of the carboxylic acid stream into an ester.

4. The method for preparing an alkyl carboxylic acid ester according to above 1, wherein the esterifying in the main reactor comprises converting an unreacted carboxylic acid stream into an ester in the preliminary reactor.

5. The method for preparing an alkyl carboxylic acid ester according to above 1, wherein an ester conversion in the preliminary reactor is 50 to 80%, and an ester conversion in the main reactor is 95% or more.

6. The method for preparing an alkyl carboxylic acid ester according to above 2, wherein the carboxylic acid stream comprises lactic acid, the first alcohol stream and the second alcohol stream comprise ethanol, and the alkyl carboxylic acid ester comprises ethyl lactate.

7. The method for preparing an alkyl carboxylic acid ester according to above 6, wherein ethanol and water are at least partially separated and removed from the top of the distillation column, and partially converted ethyl lactate and lactic acid are discharged from the bottom of the distillation column.

8. The method for preparing an alkyl carboxylic acid ester according to above 6, wherein the reaction in the preliminary reactor further comprises hydrolysis of an agglomerate comprising a dimer, a trimer or an oligomer produced from the lactic acid.

9. The method for preparing an alkyl carboxylic acid ester according to above 1, wherein the first alcohol stream has lower purity than the second alcohol stream.

10. The method for preparing an alkyl carboxylic acid ester according to above 2, further comprising refluxing alcohol removed from the first reaction product in the distillation column into the first alcohol stream.

11. The method for preparing an alkyl carboxylic acid ester according to above 1, further comprising refluxing remaining alcohol after the reaction in the main reactor into the first alcohol stream.

12. An apparatus for preparing an alkyl carboxylic acid ester, comprising: a preliminary reactor for partial esterification through reaction of a carboxylic acid with an alcohol; a separator for receiving a reaction product from the preliminary reactor and at least partially separating water and alcohol; a main reactor for receiving a reaction product from which water and alcohol are separated from a distillation column and esterifying an unreacted carboxylic acid; and a separation and purification unit for collecting an alkyl carboxylic acid ester produced from the main reactor.

13. The apparatus for preparing an alkyl carboxylic acid ester according to above 12, wherein the separator is a distillation column.

14. The apparatus for preparing an alkyl carboxylic acid ester according to above 12, further comprising: a carboxylic acid supply passage and a first alcohol supply passage, connected with the preliminary reactor; and a second alcohol supply passage connected with the main reactor.

15. The apparatus for preparing an alkyl carboxylic acid ester according to above 13, further comprising a reflux unit for recovering water and alcohol separated from the distillation column.

According to the preparation method and the preparation apparatus of an alkyl carboxylic acid ester according to embodiments of the present invention, for example, a preliminary reactor may be disposed at the front of a main reactor including a reactive distillation reactor, and preliminary conversion or partial conversion of an alcohol and a carboxylic acid may be performed. Accordingly, the degradation of selectivity by the overload in the main reactor may be prevented, and the efficiency of a process at the latter part may be improved.

In addition, through hydrolysis in the preliminary reactor, the purity and selectivity of an ester product may be improved by decomposing an agglomerate such as a dimer, a trimer, and an oligomer, produced from lactic acid and by removing impurities in advance.

In addition, by performing partial conversion in the preliminary reactor, the purity of an alcohol used may be relatively reduced, and economic feasibility of a process may be additionally improved.

According to exemplary embodiments, water and alcohol included in a first reaction product after performing partial esterification reaction in the preliminary reactor may be at least partially removed through a distillation column. Accordingly, though the preparation reaction of an alkyl carboxylic acid ester by the preliminary reactor and the main reactor is repeatedly performed, the excessive injection of water, etc., produced in the preliminary reactor into the main reactor may be prevented, and the damage of an acid catalyst, etc., carried in the main reactor may be prevented. In addition, a reaction area in the main reactor may increase, and the whole process yield and stability of an alkyl carboxylic acid ester process may be improved.

In addition, after removing alcohol with low purity, which has been injected in the preliminary reactor but not participated in partial esterification reaction, together with water through the distillation column, an alcohol with high purity may be directly injected into the main reactor. Accordingly, the concentration of an alcohol in the reaction product increases, the equilibrium of the preparation reaction of ethyl lactate moves toward a product direction, and the conversion of lactic acid and the selectivity of ethyl lactate may be improved.

DETAILED DESCRIPTION

Hereinafter, preferred embodiments of the present invention will be suggested, but the embodiments are only illustrations of the present invention and do not limit the attached claims. It is apparent that a person skilled in the art may make various changes and modifications on the embodiments within the scope of the present invention and technical spirit, and such modifications and changes are definitely included in the attached claims.

The term "alkyl carboxylic acid ester" used in the present disclosure refers to the esterification reaction product of a carboxylic acid and an alkyl alcohol. According to exemplary embodiments of the present invention, lactic acid may be used as the carboxylic acid, and ethanol may be used as the alkyl alcohol. In this case, ethyl lactate may be obtained as the alkyl carboxylic acid ester.

However, the scope of the present invention is not always limited to the preparation method and preparation apparatus of ethyl lactate, and may be expanded to a method and apparatus for esterifying diverse carboxylic acids and alkyl alcohols.

Figure 1:
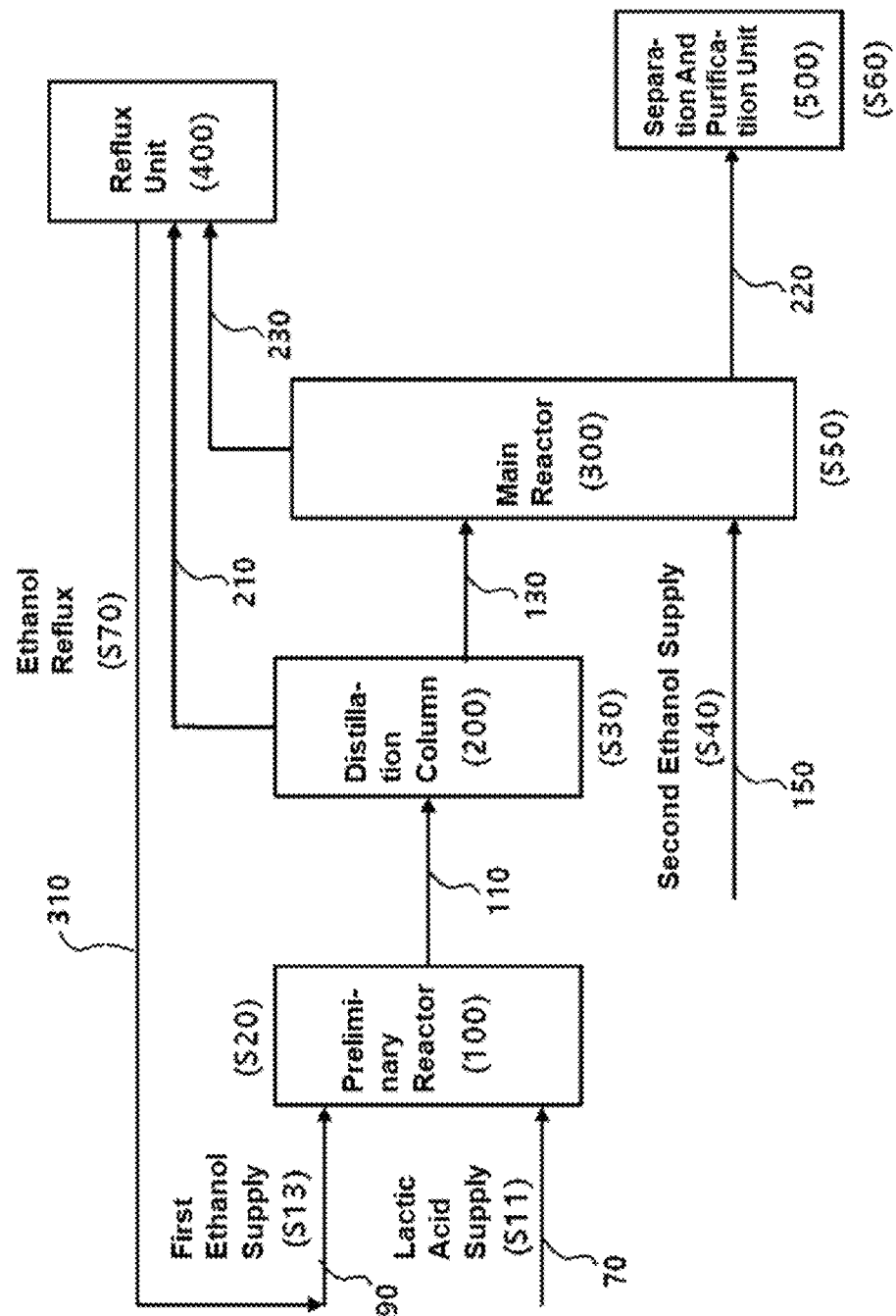
FIG. 1 is a flowchart for explaining a preparation apparatus and a preparation method of an alkyl carboxylic acid ester according to exemplary embodiments.

FIG. 1 is a flowchart for explaining a preparation apparatus and a preparation method of an alkyl carboxylic acid ester according to exemplary embodiments of the present invention. FIG. 1 illustrates a preparation apparatus, and a preparation method of ethyl lactate wherein lactic acid is used as a carboxylic acid, and ethanol is used as an alkyl alcohol.

Referring to FIG. 1, the apparatus for preparing an alkyl carboxylic acid ester according to exemplary embodiments may include a preliminary reactor (100), a distillation column (200), a main reactor (300), a reflux unit (400) and a separation and purification unit (500).

The preliminary reactor (100) may be connected with a carboxylic acid supply passage (70) and a first alcohol supply passage (90). Through the carboxylic acid supply passage (70), a lactic acid stream may be supplied into the preliminary reactor (100) (for example, step S11). Through the first alcohol supply passage (90), a first ethanol stream may be supplied into the preliminary reactor (100) (for example, step S13). The supply of the lactic acid stream and the supply of the first ethanol stream may be performed at the same time or in order.

The first ethanol stream may have lower purity than a second ethanol stream which will be explained later. In some embodiments, the purity of the first ethanol stream may be about 80 to 97%. In an embodiment, the purity of the first ethanol stream may be about 80 to 95%. In an embodiment, the purity of the first ethanol stream may be about 80 to 90%.

The term "purity" used in this disclosure may mean wt % of a target material based on the total weight. For example, ethanol with purity of 80% may mean a mixture of 20 wt % of water and 80 wt % of ethanol.

Lactic acid may be a fermentation product using microorganism. For example, lactic acid may be obtained by saccharifying starch, sugar, cellulose, algae, other organic products and then, fermenting the saccharified product through fermentable lactic acid by microorganism.

Accordingly, the lactic acid stream supplied to the preliminary reactor (101) may include various bio by-products including the microorganism, proteins, cells, minerals, etc.

According to exemplary embodiments, the preliminary reactor (100) may include a guard reactor. The guard reactor may include a solid acid catalyst bed, and in an embodiment, the solid acid catalyst may include silica, zeolite, and amberlyst-based catalysts.

In the preliminary reactor (100), preliminary esterification reaction of ethanol included in the first ethanol stream and lactic acid included in the lactic acid stream may be performed (for example, step S20). In some embodiments, the temperature of the preliminary esterification reaction may be about 70 to 110° C., preferably, about 80 to 100° C.

In the preliminary reactor (100), lactic acid may be partially converted into ethyl lactate by the preliminary esterification. According to exemplary embodiments, partial conversion in the preliminary reactor (100) may be about 50 to 80%.

If the partial conversion in the preliminary reactor (100) is less than about 50%, reaction load in the main reactor (200) which will be explained later, increases excessively, and the acquisition of ethyl lactate with desired selectivity and purity may become difficult. If the partial conversion is greater than about 80%, esterification in the preliminary reactor (100) may increase excessively, and overall process efficiency may be degraded.

In some embodiments, hydrolysis may be performed in the preliminary reactor (100) at the same time. Hydrolysis may be carried out by water contained in the first ethanol stream and the lactic acid stream, and may be carried out by water produced according to the preliminary esterification reaction in the preliminary reactor.

According to exemplary embodiments, a lactic acid agglomerate may be decomposed by the hydrolysis. The lactic acid agglomerate may include the dimer, trimer, or oligomer of lactic acid molecules. If a large amount of a lactic acid agglomerate is included in the lactic acid stream, the selectivity of ethyl lactate may be reduced, the load in the main reactor (200) or separation and purification unit (500) may increase, and overall process efficiency may be reduced.

In an embodiment, through the solid acid catalyst included in the preliminary reactor (100) for promoting the partial esterification, the hydrolysis in the preliminary reactor (100) may be promoted at the same time through the solid acid catalyst.

According to exemplary embodiments of the present invention, together with the preliminary esterification or partial conversion, the hydrolysis of a lactic acid agglomerate is carried out in the preliminary reactor (100), selectivity in the main reactor (300) or the separation and purification unit (500) may increase, and the size of the separation and purification unit (500) may be reduced.

After the partial conversion in the preliminary reactor (100), a stream (for example, a first reaction product) may be supplied to a distillation column (200) through a first reaction product passage (110). The stream after the partial conversion (for example, the first reaction product) may include partially converted ethyl lactate, unreacted lactic acid in the lactic acid stream, unreacted ethanol in the first ethanol stream and extra water.

In the distillation column (200), the unreacted ethanol and extra water included in the first reaction product which is supplied from the preliminary reactor (100) through the first reaction product passage (110) may be at least partially removed (for example, step S30).

In some embodiments, the removal or separation of ethanol and water through the distillation column (200) may be performed so that the contents of ethanol and water in a second reaction product supplied to the main reactor (300) may be about 1 wt % or less, respectively.

For example, the distillation column (200) may include a vacuum distillation column or a low-pressure distillation column. The temperature and pressure of the distillation column (200) may be controlled so that water and ethanol may be selectively distilled, for example, to conditions of a pressure of about 0.1 to 1 bar and a temperature of about 90 to 110° C.

For example, ethanol and water may be separated and removed from the top of the distillation column (200), and partially converted ethyl lactate and lactic acid may be discharged from the bottom of the distillation column (200).

For example, ethanol and water have lower boiling points than the partially converted ethyl lactate and lactic acid, and thus, may be removed from the top of the distillation column (200).

As described above, a second reaction product from which ethanol and water are at least partially removed may be discharged from the distillation column (200) and supplied to the main reactor (300). The second reaction product includes partially converted ethyl lactate and unreacted lactic acid in the preliminary reactor (100) and may include extra or small amounts of ethanol and water. As described above, in an embodiment, the second reaction product may include 1 wt % or less of ethanol and water, respectively.

Since water produced as by-products of the partial esterification reaction in the preliminary reactor (100) is removed through the distillation column (200), the damage of a catalyst in the main reactor (300) may be prevented. In addition, the hindering of the reaction site of the main reactor (300) by water may be prevented, and a sufficient esterification reaction area may be secured.

According to exemplary embodiments, the main reactor (300) may include a single reactive distillation column. Since the partial esterification is carried out in the preliminary reactor (100), the number of columns of the main reactor (300), or a process load may be reduced. In some embodiments, the main reactor (300) may include multiple reactive distillation columns connected in series or in parallel.

The reactive distillation column may be charged with, for example, a medium carrying a catalyst such as a solid acid catalyst. For example, an ion exchange resin including a sulfonic acid group may be charged in the reactive distillation column. The ion exchange resin may include, for example, polysiloxane, polystyrene, polydivinylbenzene, etc. The ion exchange resin may be surface treated with, for example, a metal such as zirconium and titanium, or oxides thereof.

In the main reactor (300), unreacted lactic acid included in a stream after the partial conversion (for example, a first reaction product) may undergo esterification reaction with ethanol to be converted into ethyl lactate (for example, step S50).

According to exemplary embodiments, ethyl lactate conversion of about 95% or more may be obtained in the main reactor (300). In an embodiment, ethyl lactate conversion of about 98% or more may be obtained in the main reactor (300), preferably, ethyl lactate conversion of substantially 100% may be obtained.

In some embodiments, the temperature of the esterification reaction in the main reactor (300) may be about 70 to 110° C., preferably, 80 to 100° C.

In some embodiments, a second ethanol stream may be supplied into the main reactor (300) (for example, step S40). For example, the second ethanol stream may be supplied to the main reactor (300) through a separately connected second alcohol supply passage (150).

The second ethanol stream may have higher purity than the first ethanol stream introduced into the preliminary reactor (100), and as described above, a portion of lactic acid may be partially converted using a first ethanol stream with relatively lower purity in the preliminary reactor (100). By partially converting a portion of lactic acid using the first ethanol stream with relatively lower purity in the preliminary reactor (100), the amount used of costly ethanol with high purity may be reduced while maintaining the desired selectivity of ethyl lactate, and economic feasibility and efficiency of overall process may be improved.

In exemplary embodiments, the purity of the second ethanol stream may be about 95% or more, preferably, about 99% or more. By increasing the purity of ethanol directly introduced into the main reactor (300), the equilibrium of the preparation reaction of ethyl lactate moves toward a product, and the selectivity of ethyl lactate obtained may be improved.

In addition, since unreacted first ethanol stream with low purity among the first reaction product produced from the preliminary reactor (100) is removed together with water through the distillation column (200), the selectivity of esterification reaction through the second ethanol stream with high purity, which is directly introduced into the main reactor (300) may be improved, and the equilibrium of esterification reaction may be promoted toward a product direction. Accordingly, the conversion of lactic acid and the selectivity of ethyl lactate may be additionally improved.

For example, from the bottom of the main reactor (300), a stream after main reaction (for example, a third reaction product) may be introduced through a third reaction product passage (220) to the separation and purification unit (500).

As described above, by performing partial esterification by continuously supplying ethanol with relatively low purity through a reflux unit to the preliminary reactor (100), and separately supplying ethanol with high purity to the main reactor (300), the economic feasibility and efficiency of a whole process may be improved, and the selectivity of ethyl lactate and the conversion of lactic acid may be improved.

In the separation and purification unit (500), a process for concentrating and/or collecting a target ester from the stream after main reaction (for example, a third reaction product) produced in the main reactor (300) may be performed (for example, step S60). According to exemplary embodiments, the separation and purification unit (500) may be positioned at the rear of the main reactor (300) and may concentrate and/or collect the target ester.

In some embodiments, the separation and purification unit (500) may include a distillation unit (for example, vacuum distillation column). As described above, from a third reaction product passage (220) connected with the bottom of the main reactor (300), the product after main reaction (for example, third reaction product) may be supplied to the distillation unit.

The product after main reaction (for example, the third reaction product) may include ethyl lactate produced from the main reactor (300), remaining ethanol and by-products. For example, the by-products may include an agglomerate including a dimer, trimer or oligomer produced from lactic acid, bio-derived residues, etc. As described above, the by-products may be at least partially decomposed through hydrolysis in the preliminary reactor (100), and the amount of the by-products in the product after the reaction may be markedly reduced.

Among the products after the reaction, ethyl lactate having a low boiling point may be taken out from the top of the vacuum distillation column and obtained as a target ester. Among the products after the reaction, the by-products having high boiling points may be taken out from the bottom of the vacuum distillation column and removed.

As explained referring to FIG. 1, agglomerates such as the dimer, trimer and oligomer of lactic acid are preliminarily decomposed or removed through hydrolysis in the preliminary reactor (100), and the process load of subsequent processes may be reduced. Accordingly, additionally performed subsequent processes, for example, an ester hydrolysis and/or transesterification (TE) unit may be removed, or their sizes may be reduced to increase process efficiency.

In some embodiments, in the distillation column (200) and/or main reactor (300), remaining ethanol and water produced may be supplied to the reflux unit (400). For example, as described above, ethanol and water separated and removed from the first reaction product through the distillation column (200) may be supplied through a first alcohol collection passage (210) to the reflux unit (400). The remaining ethanol and water produced as the by-products of the esterification reaction in the main reactor (300) may be supplied through a second alcohol collection passage (230) to the reflux unit (400).

According to exemplary embodiments, the reflux unit (400) may include a distillation column or a distillation drum. Through the reflux unit (400), water may be at least partially removed, and concentrated ethanol may be refluxed through a reflux passage (310) to the preliminary reactor (100) to be combined with a first ethanol stream (for example, step S70). The reflux stream supplied through the reflux passage (310) may have substantially the same purity as the first ethanol stream.

Hereinafter, the method for preparing an alkyl carboxylic acid ester according to embodiments of the present invention will be explained in detail referring to particular experimental embodiments. Embodiments and comparative embodiments included in the experimental embodiments are only illustrations of the present invention but do not limit the attached claims. It is apparent that a person skilled in the art may make various changes and modifications on the embodiments within the scope of the present invention and technical spirit, and such modifications and changes are definitely included in the attached claims.

EXAMPLES

1) Conversion into Ethyl Lactate in Preliminary Reactor 88 wt % of lactic acid (LA) and 80 wt % of ethanol (EtOH) were mixed and used as a feed of a preliminary reactor. The molar ratio of the lactic acid and the ethanol was controlled to 1:1. The lactic acid used a bio-derived product produced from a fermentation process.

Figure 2:
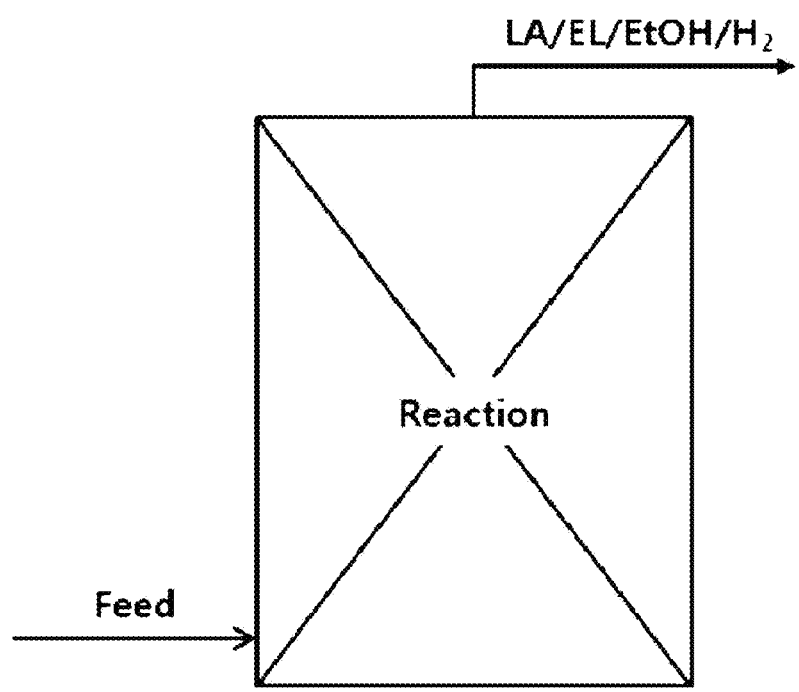
FIG. 2 is a cross-sectional view showing the schematic structure and operation of a preliminary reactor according to exemplary embodiments.

In a preliminary reactor having a single bed type charged with a solid acid catalyst, as shown in FIG. 2, esterification reaction was performed at a temperature of about 80° C. under an air pressure to produce a first reaction product.

The first reaction product included 32 wt % of ethanol, 32 wt % of ethyl lactate, 20 wt % of water, and 16 wt % of lactic acid and other by-products.

2) Removal of Ethanol and Water from Distillation Column

Figure 3:
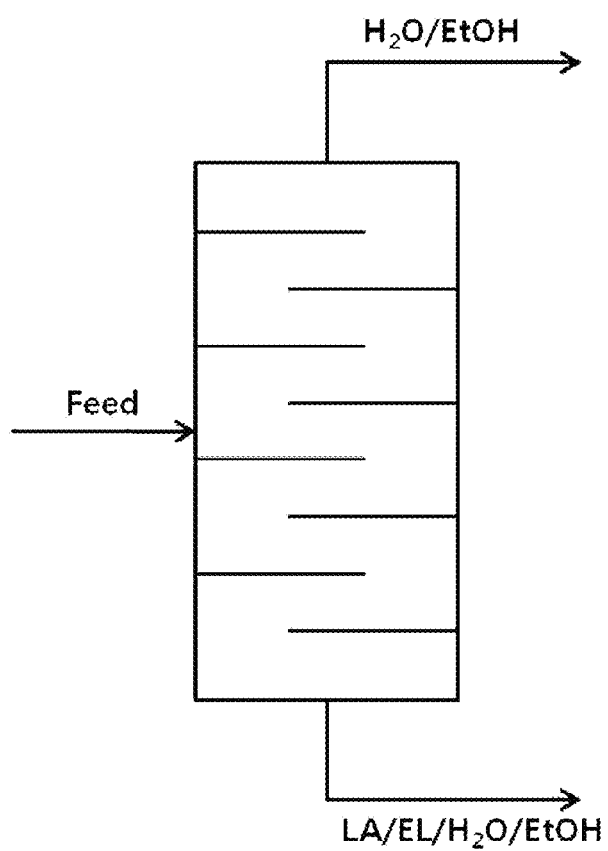
FIG. 3 is a cross-sectional view showing the schematic structure and operation of a distillation column according to exemplary embodiments.

The partially converted first reaction product into ethyl lactate through the preliminary reactor was used as the feed of a distillation column. As shown in FIG. 3, a vacuum distillation column was used as a vacuum column. In the vacuum distillation column, a distillation process was performed under conditions of a pressure of −0.9 bar (gauge) and a temperature of 125° C.

From the top of the vacuum distillation column, water and alcohol in gas states were exhausted, and from the bottom, a second reaction product including ethyl lactate, lactic acid, ethanol, and water was discharged. The second reaction product discharged from the bottom included 40 wt % of ethyl lactate, 58 wt % of lactic acid, 1 wt % of ethanol and 1 wt % of water.

3) Conversion into Ethyl Lactate in Main Reactor

Figure 4:
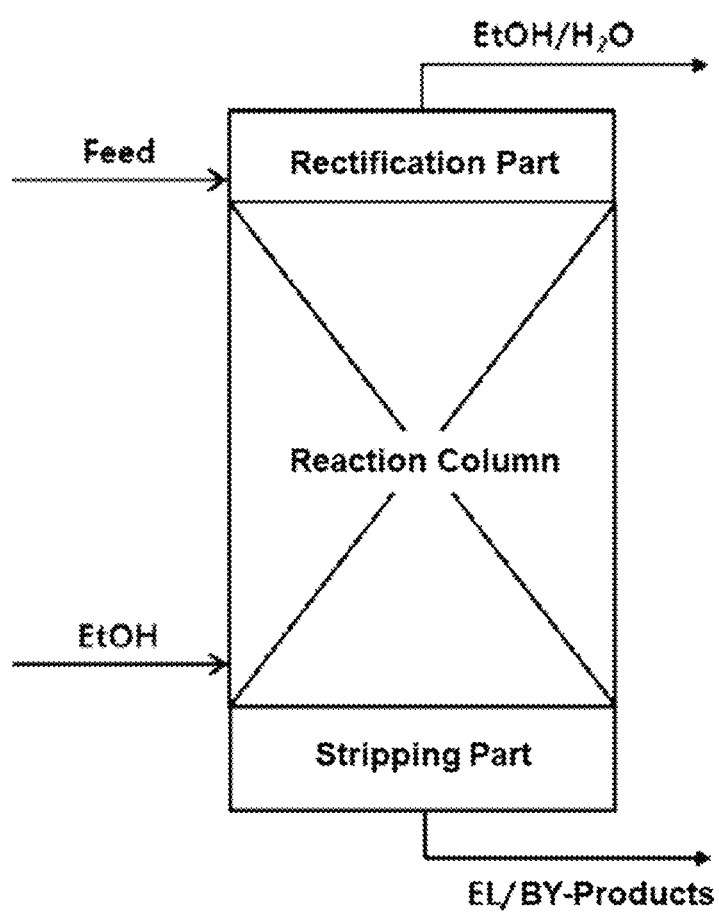
FIG. 4 is a cross-sectional view showing the schematic structure and operation of a main reactor according to exemplary embodiments.

The second reaction product from which water and ethanol were at least partially removed through the vacuum distillation column, was used as the feed of the main reactor. A reactive distillation (RD) column charged with a solid acid catalyst was used as a main reactor (see FIG. 4).

The second reaction product was injected into the top of the main reactor, and 99% ethanol was injected into the bottom of the main reactor, respectively, and esterification reaction was completed at the temperature of about 80° C. and under an air pressure. The volume ratio of the feed and ethanol injected was controlled to 1:0.5.

A product obtained from the bottom of the main reactor column (stripping part, see FIG. 4) was cooled by a cooling apparatus, and a liquid composition was measured using Agilent 7890 restek RTx-VRX GC Column for the flame ionization detectors (FIDS).

Figure 5:
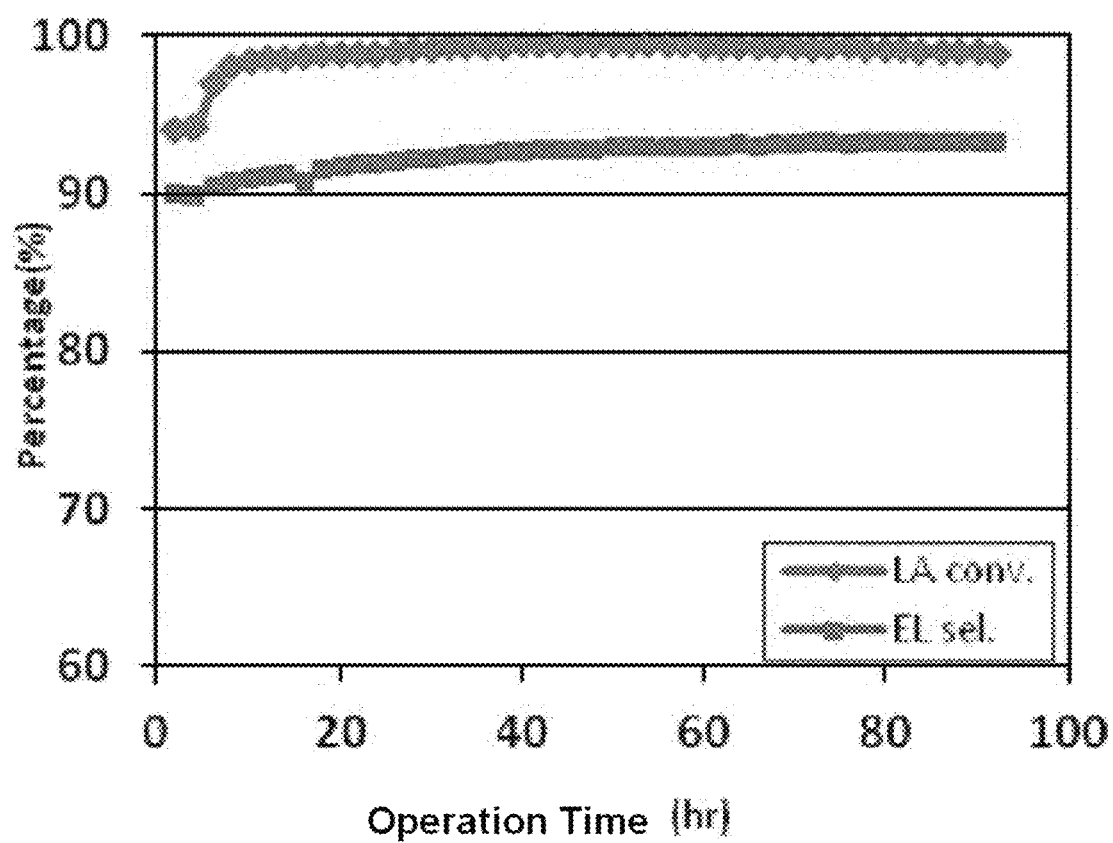
FIG. 5 is a graph showing the conversion of lactic acid and the selectivity of ethyl lactate in accordance with the operation time of a preparation process of ethyl lactate according to an exemplary embodiment.

The preparation process of ethyl lactate according to an embodiment was repeatedly performed, and the composition of a product obtained from the bottom of the main reactor column was measured. Based on the composition data of the product, a graph showing the conversion of lactic acid (LA) and the selectivity of ethyl lactate (EL) in accordance with the operation time of the preparation process of ethyl lactate is shown in FIG. 5.

Comparative Example

The same preparation process of ethyl lactate as in the Example was performed except for not performing the removing process of ethanol/water in the distillation column.

The preparation process of ethyl lactate according to a comparative embodiment was repeatedly performed, and the composition of a product obtained from the bottom of the main reactor column was measured. Based on the composition data of the product, a graph showing the conversion of lactic acid (LA) and the selectivity of ethyl lactate (EL) in accordance with the operation time of the preparation process of ethyl lactate is shown in FIG. 6.

Figure 6:
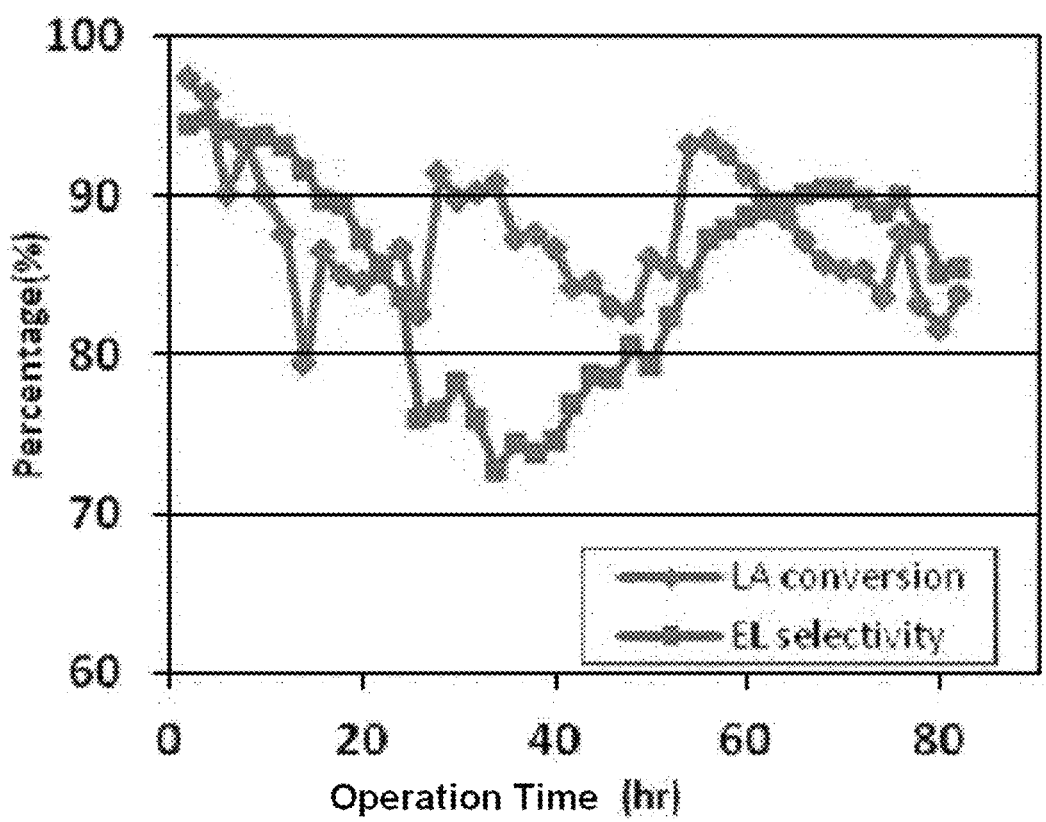
FIG. 6 is a graph showing the conversion of lactic acid and the selectivity of ethyl lactate in accordance with the operation time of a preparation process of ethyl lactate according to an exemplary comparative embodiment.

Referring to FIG. 5 and FIG. 6, the conversion of lactic acid and the selectivity of ethyl lactate were increased overall in the Example and Comparative Example, undergone the preliminary reactor at the initiation stage of the reaction.

Through this, it could be found that both load and reaction efficiency in the main reactor were improved by the hydrolysis of lactic acid agglomerates in advance through partial esterification utilizing a guard reactor prior to the main reaction.

However, in case of the Example undergone the distillation column after the preliminary reactor, the lactic acid conversion (LA conversion) and the ethyl lactate selectivity (EL selectivity) in accordance with the operation time were maintained constant, though the preparation process of ethyl lactate was repeatedly performed, when compared to the Comparative Example.

Through this, it could be found that in case of removing water and ethanol through the distillation column after the preliminary reactor before injecting the reaction product to the main reactor, the damage of an acid catalyst carried in the main reactor was prevented, a reaction area for converting into ethyl lactate was increased, and an overall process yield and stability were improved.

What is claimed is:

1. A method for preparing an alkyl carboxylic acid ester, the method comprising:
    reacting a carboxylic acid stream and a first alcohol stream in a first reactor to produce a first reaction product;
    at least partially removing alcohol and water from the first reaction product through a distillation column to produce a second reaction product;
    esterifying by reacting the second reaction product with a second alcohol stream in a second reactor; and
    recovering an alkyl carboxylic acid ester from the second reactor,
    wherein the carboxylic acid stream comprises lactic acid, the first alcohol stream and the second alcohol stream comprise ethanol, and the alkyl carboxylic acid ester comprises ethyl lactate.

2. The method for preparing an alkyl carboxylic acid ester according to claim 1, wherein the production of the first reaction product in the first reactor comprises converting a portion of the carboxylic acid stream into an ester.

3. The method for preparing an alkyl carboxylic acid ester according to claim 1, wherein the esterifying in the second reactor comprises receiving an unreacted carboxylic acid stream remaining in the first reactor to convert an unreacted carboxylic acid of the unreacted carboxylic acid stream into an ester in the first second reactor.

4. The method for preparing an alkyl carboxylic acid ester according to claim 1, wherein an ester conversion in the first reactor is 50 to 80%, and an ester conversion in the second reactor is 95% or more.

5. The method for preparing an alkyl carboxylic acid ester according to claim 1, wherein ethanol and water are at least partially separated and removed from the top of the distillation column, and partially converted ethyl lactate and lactic acid are discharged from the bottom of the distillation column.

6. The method for preparing an alkyl carboxylic acid ester according to claim 1, wherein the reaction in the first reactor further comprises hydrolysis of an agglomerate comprising a dimer, a trimer or an oligomer produced from the lactic acid.

7. The method for preparing an alkyl carboxylic acid ester according to claim 1, wherein the first alcohol stream has lower purity than the second alcohol stream.

8. The method for preparing an alkyl carboxylic acid ester according to claim 1, further comprising refluxing the alcohol removed from the first reaction product in the distillation column into the first alcohol stream.

9. The method for preparing an alkyl carboxylic acid ester according to claim 1, further comprising refluxing remaining alcohol after the reaction in the second reactor into the first alcohol stream.

* * * * *